United States Patent

Korsunsky

(10) Patent No.: US 7,844,028 B2
(45) Date of Patent: Nov. 30, 2010

(54) X-RAY DIFFRACTION METHOD

(75) Inventor: Alexander M. Korsunsky, Oxford (GB)

(73) Assignee: Isis Innovation Limited, Oxford (GB)

( * ) Notice: Subject to any disclaimer, the term of this patent is extended or adjusted under 35 U.S.C. 154(b) by 1021 days.

(21) Appl. No.: 10/502,432

(22) PCT Filed: Jan. 24, 2003

(86) PCT No.: PCT/GB03/00283

§ 371 (c)(1),
(2), (4) Date: Jul. 25, 2005

(87) PCT Pub. No.: WO03/062805

PCT Pub. Date: Jul. 31, 2003

(65) Prior Publication Data

US 2006/0176998 A1   Aug. 10, 2006

(30) Foreign Application Priority Data

Jan. 25, 2002   (GB)   .................. 0201773.9

(51) Int. Cl.
*G01N 23/207* (2006.01)
*G01N 23/20* (2006.01)
(52) U.S. Cl. .............. 378/73; 378/70; 378/74
(58) Field of Classification Search ........ 378/70–78, 378/84, 85
See application file for complete search history.

(56) References Cited

U.S. PATENT DOCUMENTS

| 4,284,887 | A | * | 8/1981 | Kusumoto et al. ........... 378/82 |
| 4,364,122 | A | * | 12/1982 | Wolfel et al. ................. 378/73 |
| 4,561,062 | A | * | 12/1985 | Mitchell ...................... 702/40 |
| 4,916,720 | A | * | 4/1990 | Yamamoto et al. ........... 378/81 |
| 5,265,144 | A | | 11/1993 | Harding et al. |
| 5,589,690 | A | * | 12/1996 | Siewert et al. .......... 250/390.06 |
| 5,787,145 | A | | 7/1998 | Geus |
| 5,878,106 | A | * | 3/1999 | Fujiwara ....................... 378/79 |
| 6,072,853 | A | * | 6/2000 | Hall ............................ 378/73 |

(Continued)

FOREIGN PATENT DOCUMENTS

DE   203394 A1   10/1983

(Continued)

OTHER PUBLICATIONS

Canberra, Capabilities Profile, Apr. 2002, Canberra, Inc., pp. 1-24.*

(Continued)

*Primary Examiner*—Edward J Glick
*Assistant Examiner*—Anastasia Midkiff
(74) *Attorney, Agent, or Firm*—McCarter & English, LLP

(57) ABSTRACT

An X-ray diffraction method for the analysis of polycrystalline materials, the method comprising: (a) providing a polycrystalline material for analysis; (b) providing a polychromatic X-ray source, wherein the source produces X-rays by accelerating charged particles to energies of no more than 1 MeV; (c) collimating X-rays from the polychromatic X-ray source into a beam having a divergence in the range of from $10^{-4}$ to $10^{-2}$ radians; (d) exposing at least a portion of the polycrystalline material to the collimated X-ray beam, whereby the beam is diffracted; (e) collecting at least some of the diffracted X-rays in an energy dispersive X-ray detector or array; and (f) analysing the collected, diffracted X-rays.

24 Claims, 4 Drawing Sheets

U.S. PATENT DOCUMENTS 6,269,144 B1 * 7/2001 Dube et al. .................... 378/71
7,065,175 B2 * 6/2006 Green ......................... 378/57
2003/0012334 A1 * 1/2003 Kurtz et al. .................. 378/73

FOREIGN PATENT DOCUMENTS

| EP | 0 354 045 A2 | 7/1990 |
|---|---|---|
| GB | 2299251 | 9/1996 |
| WO | WO 91/08372 | * 11/1990 |

OTHER PUBLICATIONS

Canberra, Germanium Detectors, Jan. 2003, Canberra, Inc. pp. 1-3.*

* cited by examiner

X-RAY DIFFRACTION METHOD

RELATED APPLICATIONS

This application is a National Stage of International Application No. PCT/GB03/00283, filed Jan. 24, 2003, which claims the benefit of Great Britain Application No. 0201773.9, filed Jan. 25, 2002.

The present invention relates to the field of X-ray diffraction of crystalline materials and, in particular, to an X-ray diffraction method for the determination of structural and/or chemical characteristics of polycrystalline engineering materials and components formed therefrom.

X-rays are electromagnetic radiation having a wave length of from $10^{-11}$ to $10^{-9}$ m and produced by bombardment of atoms by high-quantum-energy particles. In practice, X-rays may be produced by bombarding a metal target, for example copper or tungsten, with fast electrons in a vacuum tube.

The principle of X-ray generation in a vacuum tube is schematically illustrated in FIG. 1. Electrons are emitted by the heated cathode (Ca) and accelerated by the applied voltage towards the anode (or anti-cathode, Ac) target. There they undergo rapid deceleration and absorption processes, which result in the emission of X-rays.

The radiation emitted as a result of the collision between electrons and the metal target can be separated into two components: (i) a continuous spectrum, which is spread over a wide range of wavelengths (also known as Bremsstrahlung); and (ii) a superimposed line spectrum, which is determined by the materials of the target (also known as the characteristic radiation).

The use of X-ray diffraction is of great importance in the analysis of crystals. For example, in the fields of metallurgy and materials science, X-ray diffraction techniques may be used to identify the lattice parameter and the structure of metal crystals. Additionally, the techniques may be used to identify the arrangement of different kinds of atoms in crystals, the presence of imperfections, the orientation of grains, the size of grains, the size and density of precipitates and the state of lattice distortion.

Known X-ray diffraction techniques include the Laue method, the rotating crystal method and the powder method (also known as the Debye/Scherrer method).

In the Laue method a stationary single crystal is bathed in a beam of polychromatic radiation. This method is used for determining the orientation of single crystals and the study of crystal imperfections.

In the rotating crystal method a single crystal is rotated in a beam of monochromatic X-rays. This method is also used for the determination of crystal structures.

In the powder method a powdered polycrystalline sample is bathed in a beam of monochromatic radiation. This method is used for the determination of lattice parameters, grain sizes and the preferred orientation of grains.

The powder method is also used to study bulk polycrystalline samples, such as engineering components and structures. For example, it can be used to determine the lattice parameter variation in orientation and position, and to deduce sample strain and stress.

Conventional laboratory diffraction measurements rely on interrogating only a thin ($\approx$<50 μm) surface layer of the sample. Accordingly, such techniques do not provide information regarding stresses and strains in sub-surface regions or in the bulk of a sample.

Another widespread application of X-rays in industry and medicine is radiography, i.e. for transmission photography to obtain absorption contrast-images. The only property of the X-ray radiation that is utilised in such applications is the penetrating ability.

In standard radiographic set-up, industrial tungsten target X-ray tubes are used to produce polychromatic radiation within a widely divergent (~40°) cone.

In defectoscopic configuration, the object of study, for example an aluminium casting, is bathed in an incident X-ray beam, and a photographic plate or CCD camera is used to record the image which registers the attenuation of the beam along the path between the source and any given pixel. This set-up is only capable of providing information on relatively large defects (typically about a millimeter in size), such as casting voids.

For the purpose of quantitative diffraction analysis, the radiation produced by an industrial X-ray tube is not well suited in that it has a definition that is too poor both in terms of wave length (energy) and wave vector (direction).

The present invention aims to address at least some of the problems associated with the prior art.

In a first aspect the present invention provides an X-ray diffraction method for the analysis of polycrystalline materials, the method comprising:
(a) providing a polycrystalline material for analysis;
(b) providing a polychromatic X-ray source, wherein the source produces X-rays by accelerating charged particles to energies of no more than 1 MeV;
(c) collimating X-rays from the polychromatic X-ray source into a beam having a divergence in the range of from $10^{-4}$ to $10^{-2}$ radians;
(d) exposing at least a portion of the polycrystalline material to the collimated X-ray beam, whereby the beam is diffracted;
(e) collecting at least some of the diffracted X-rays; and
(f) analysing the collected, diffracted X-rays.

The following discussion applies to all aspects of the present invention unless otherwise stated.

The source preferably produces X-rays by accelerating charged particles to energies of no more than 500 keV, more preferably to no more than 400 keV, still more preferably to no more than 300 keV. The source will typically comprise means to accelerate electrons in a vacuum tube to impact a metal target.

The X-ray beam typically has a brilliance $\leq 10^{12}$ photons/s/mm$^2$/mrad$^2$/0.1% BW.

The diffracted X-rays may suitably be collected by an energy dispersive X-ray detector or array. For example, a Li-drifted Si or Ge solid state detector may be used. The energy dispersive X-ray detector typically has a relative energy resolution of $0.5 \times 10^{-2}$ to $4 \times 10^{-2}$, more typically $1 \times 10^{-2}$ to $3 \times 10^{-2}$. An example of a suitable detector is the Canberra BEGe liquid nitrogen cooled, solid state energy dispersive germanium crystal X-ray and gamma-ray detector, in combination with multi-channel analyser, computer acquisition software and hardware.

The energy of the collimated X-ray beam is preferably $\geq 60$ keV, more preferably in the range of from 100 to 300 keV. This enables the collimated X-ray beam to penetrate the polycrystalline material to a depth of typically $\geq 1$ mm, preferably $\geq 5$ mm, more preferably, $\geq 10$ mm, still more preferably $\geq 15$ mm. Indeed, the attenuation depth can be up to 50 mm or more depending on the polycrystalline material. Thus, sub-surface X-ray analysis may be achieved. The attenuation depth is the thickness of material such that the transmitted beam intensity is equal to 37% of the incident beam intensity.

As mentioned above, the X-ray source will typically comprise means to accelerate electrons in a vacuum tube to impact a metal target. In this manner, a metal target is bombarded with fast electrons. The X-ray source is preferably an industrial X-ray-source (for example a tungsten target X-ray tube) such as may be used in standard radiographic applications. A suitable example is a 160 kV, 1.6 kW industrial X-ray source (W tube) by Philips, supplied by AT Roffey Ltd (circa 1980).

The beam may be collimated using known techniques. For example, a pair of adjustable copper-tungsten X-ray slits may be used.

The method may further comprise moving the collimated X-ray beam relative to the polycrystalline material. In a preferred embodiment, the collimated X-ray beam is scanned across at least a portion of the polycrystalline material, while keeping the polycrystalline material stationary. This is advantageous in circumstances where the polycrystalline material forms part of a relatively large engineering component. In such cases, movement of the component would be difficult.

The collected, diffracted X-rays may be analysed in order to determine a structural and/or chemical characteristic of the polycrystalline material, for example lattice parameter determination. In turn, lattice parameter determination may be used to provide information on stresses and/or strains in the polycrystalline material and, preferably, to map stresses and/or strains. Stresses and/or strains in the bulk of the polycrystalline material may be mapped at a depth of typically $\geq 1$ mm, preferably $\geq 5$ mm, more preferably $\geq 10$ mm, still more preferably $\geq 15$ mm. Indeed, stresses and/or strains in the bulk of the polycrystalline material may be mapped at a depth of up to 50 mm or more depending on the polycrystalline material. This is in contrast to the conventional laboratory techniques where only a thin surface layer is analysed.

The polycrystalline material may be a natural object or an engineering article or component part thereof. The polycrystalline material will typically comprise a metal or alloy, a ceramic or a crystalline polymer or a composite crystalline material, such as, for example, a ceramic reinforced metal matrix composite material. An example is SiC reinforced Al.

The polycrystalline material will typically have a thickness of $\geq 0.1$ mm, more typically $\geq 1$ mm, still more typically $\geq 5$ mm, still more typically $\geq 10$ mm, still more typically $\geq 15$ mm. Indeed, the polycrystalline material may have a thickness of up to 50 mm or more depending on the absorption.

In contrast to the conventional powder diffraction techniques, the polycrystalline material need not be in the form of a fine grained powder, nor is material removal, cutting or drilling of any kind required within the region of interest. The method according to the present invention therefore allows engineering components to be analysed in their intended structural form. This is important for the measurement of sub-surface engineering stresses and strains.

In a second aspect, the present invention provides an apparatus for X-ray diffraction analysis of polycrystalline materials, the apparatus comprising:
(i) a polychromatic X-ray source (10), wherein the source produces X-rays by accelerating charged particles to energies of no more than 1 MeV;
(ii) means for collimating X-rays from the polychromatic X-ray source into a beam (30) having a divergence in the range of from $10^{-4}$ to $10^{-2}$ radians;
(iii) an energy dispersive X-ray detector (20) or array for collecting at least some of the diffracted X-rays resulting, in use, from exposing at least a portion of a polycrystalline material to the collimated X-ray beam; and
(iv) means for analysing the collected, diffracted X-rays (50).

The polychromatic source (10) may be moveable with respect to a polycrystalline material to be analysed. Advantageously, the collimated X-ray beam (30) is adapted, in use, to scan across the sample (40) of the polycrystalline material, while the polycrystalline material is maintained stationary.

In the method and apparatus according to the present invention the polycrystalline material (for example a component or sample) is preferably maintained stationary, while an X-ray probe is moved around it. The probe may comprise the X-ray source and the detector, which may be fixed relative to each other on a rigid arm.

In a third aspect, the present invention provides a method of quantitatively mapping the sub-surface distribution of the crystal lattice parameter in a polycrystalline material, the method comprising:
(a) providing a sample for analysis, wherein the sample comprises a polycrystalline material;
(b) providing a polychromatic X-ray source, wherein the source produces X-rays by accelerating charged particles to energies of no more than 1 MeV;
(c) collimating X-rays from the polychromatic X-ray source into a beam having a divergence in the range of from $10^{-4}$ to $10^{-2}$ radians and an attenuation length typically $\geq 1$ mm;
(d) scanning the collimated X-ray beam across the sample, whereby the beam is diffracted;
(e) collecting at least some of the diffracted X-rays in an energy dispersive X-ray detector or array; and
(f) analysing the collected, diffracted X-rays to map the lattice parameter in the polycrystalline material.

The polycrystalline material may be a natural material or, alternatively, an engineering material, including a component formed therefrom.

This method may preferably be used to determine the stresses and/or strains in polycrystalline natural or engineering materials and components formed therefrom. Accordingly, a preferred further step (f) involves transforming the map of the lattice parameter into a map of sub-surface engineering stresses and/or strains.

The technique of composite strain mapping is described in *Scripta Materialia*, Vol. 39, No. 12, pp. 1075-1712, 1988.

Typically, the present invention achieves a strain measurement accuracy of $50 \times 10^{-6}$ to $200 \times 10^{-6}$, more typically $100 \times 10^{-6}$ to $150 \times 10^{-6}$. The spatial resolution is typically, from 0.25 mm to 1 mm.

Whole pattern fitting may be applied to extract extremely accurate values of the lattice parameter (better than $5 \times 10^{-5}$) and hence residual lattice strain.

The present invention will now be described further with reference to the following drawings, in which.

EXAMPLE

Transmission polychromatic X-ray diffraction experiments were carried out on 1.5 mm thick samples of rolled Al sheet. The strain accuracy achieved (prior to optimization) was approximately $150 \times 10^{-6}$. This corresponds to a stress accuracy of $\approx 10$ MPa in aluminium, $\approx 14$ MPa in copper, and $\approx 28$ MPa in steel.

The experimental set-up comprised:
a) A 160 kV, 1.6 kW industrial X-ray source (W tube) by Philips, supplied by AT Roffey Ltd (circa 1980), placed in a lead-lined room and position-controlled remotely using a traverse motor assembly;
b) A Canberra BEGe liquid nitrogen cooled, solid state energy dispersive germanium crystal X-ray and gamma-ray detector, in combination with multi-channel analyser, computer acquisition software and hardware; and
c) A pair of adjustable (0.5 to 5 mm) composite (copper tungsten) X-ray slits.

For the purpose of spatial definition the beam was collimated using two large blocks of lead, about 50 mm thick, which only allowed radiation through a long slit, 0.5 mm wide. This set-up was used in the diffraction experiment. However, a secondary slit was needed to further define the beam direction, and also as an anti-scatter device. The two slits were aligned using a laser pointer. Similarly, a pair of slits was used on the detector side to provide directional definition. In both cases the slits were mounted at two ends of a copper tube. Copper, a good photon absorber, was used to reduce secondary scatter.

While the incident beam was close to horizontal, the diffracted beam was defined to be inclined at an angle of about 6.2°.

Figure 1:
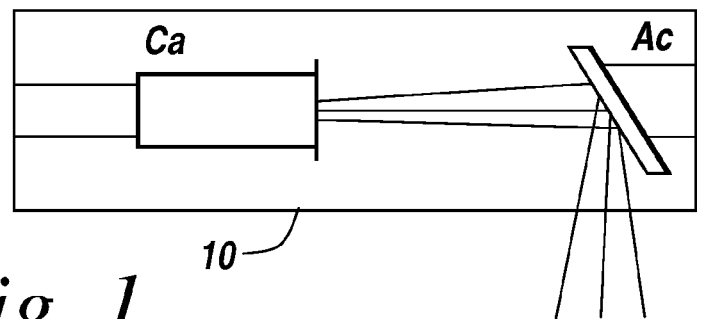
FIG. 1 is a schematic illustration of the process of X-ray generation in a vacuum tube.
Figure 2:
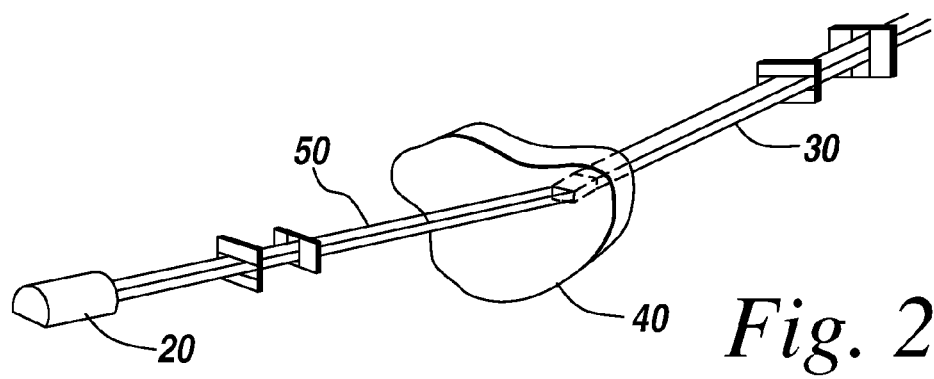
FIG. 2 shows a diffraction configuration used in the Example (from right to left: incident beam—slits—sample—slits—detector)

A schematic illustration of the set-up is shown in FIG. 2.

Figure 3:
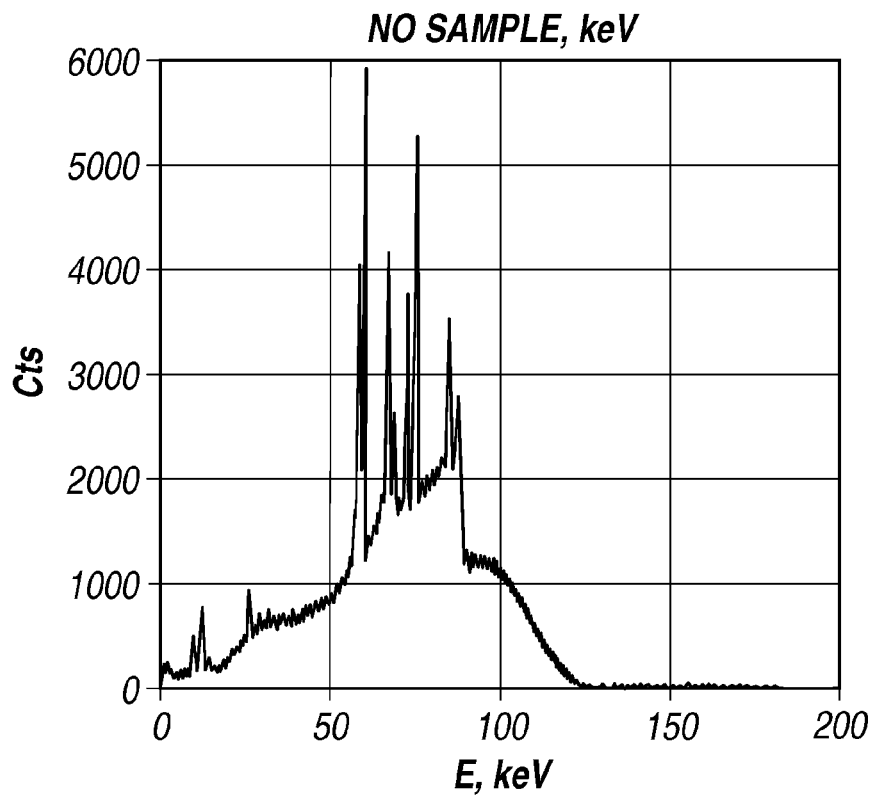
FIG. 3 shows the X-ray source spectrum (energy) used in the Example.
Figure 4:
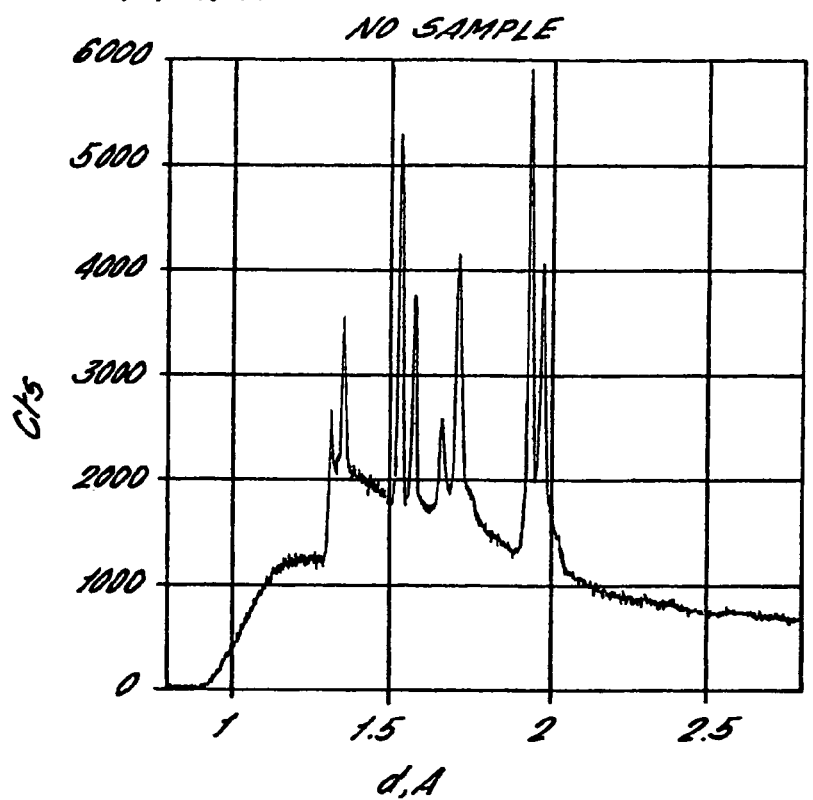
FIG. 4 shows the 'no sample' source pattern (lattice spacing) used in the Example.

The lead block surfaces were irradiated by the intense incident X-ray beam and thus fluoresced (i.e. absorbed and re-emitted X-rays) at the characteristic wavelengths (energies) of Pb. This is evidenced by the energy spectrum shown in FIG. 3. The characteristic energies present due to the 'source' properties do not change with the scattering angle prescribed by the set-up. However, the peaks of energy corresponding to diffraction from the crystal lattice of the sample depend on the scattering angle through Bragg's equation: $2 d \sin \theta = n\lambda = hc/f$. This allowed the scattering angle to be adjusted so as to avoid, as far as possible, overlap with the 'signature' peaks of lead. Given a certain scattering angle $\theta$, the energy pattern is converted to the lattice parameter pattern using Bragg's equation. For the configuration used, $\theta = 3.1°$, and the 'no sample' pattern is shown in FIG. 4.

Figure 5:
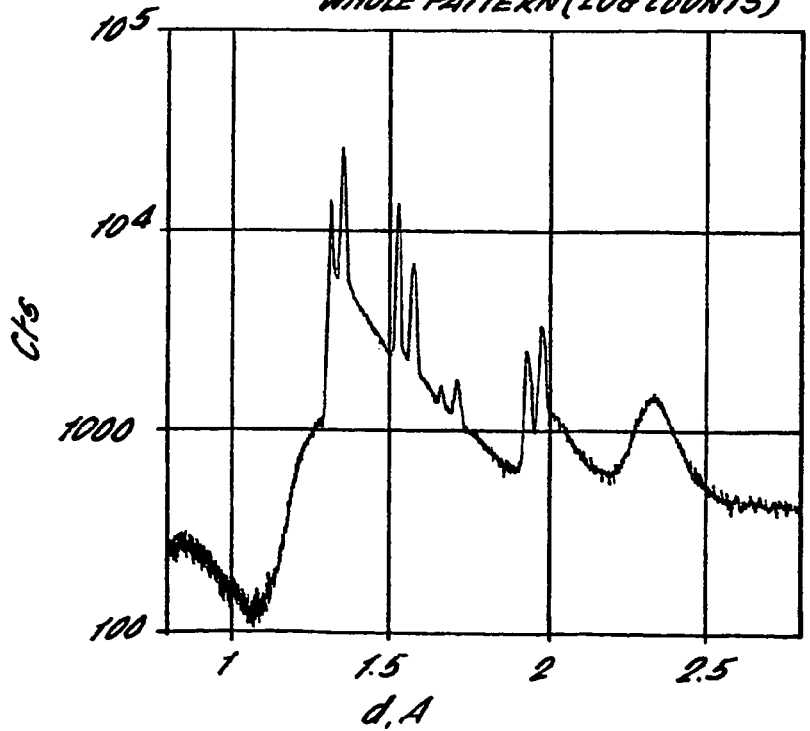
FIG. 5 shows a scattering pattern of a polycrystalline Al alloy sample used in the Example (log scale, counts)
Figure 6:
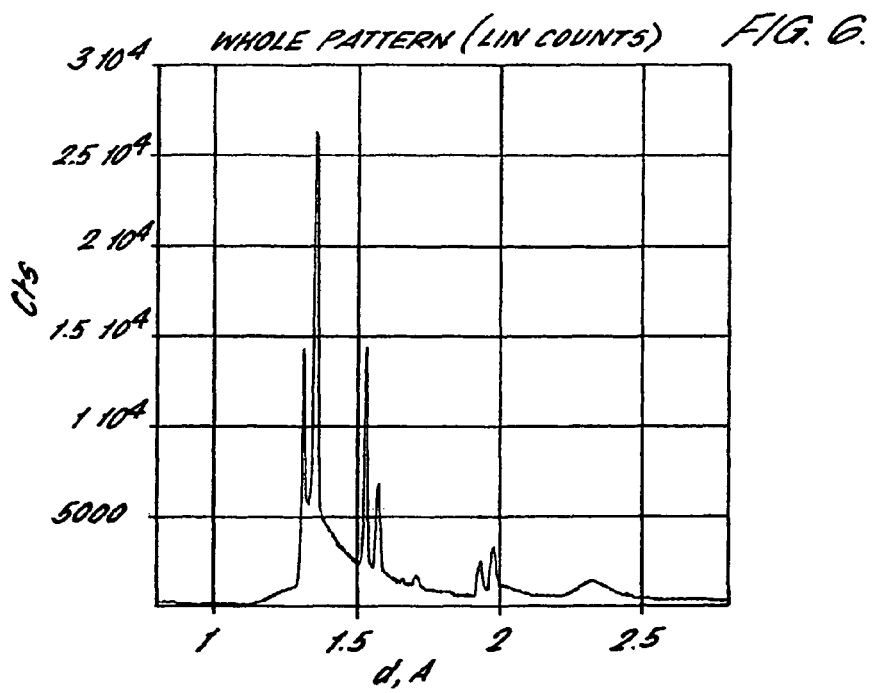
FIG. 6 shows a scattering pattern of a polycrystalline Al alloy sample used in the Example (linear scale, counts)

The sample was then placed at the intersection of the incident and scattered beams. The sample contributed to the flux into the detector, through diffraction on many individual grains. New peaks appear in the pattern. This is illustrated in FIG. 5, where a logarithmic scale is used for the vertical axis to make the peak at approximately 2.3 Å more prominent. FIG. 6 shows the same profile using a linear vertical scale for the counts.

Although the aluminium diffraction peak at approximately 2.3 Å in FIG. 6 appeared broad and small, fitting it with a simple Gaussian function demonstrated that it provided acceptable accuracy. The Gaussian peak shape used for this peak (dubbed 'Peak 1') was described by the function:

$$m2 * \exp(-(m0-m1)^2/2/m3^2) + m4$$

Figure 7:
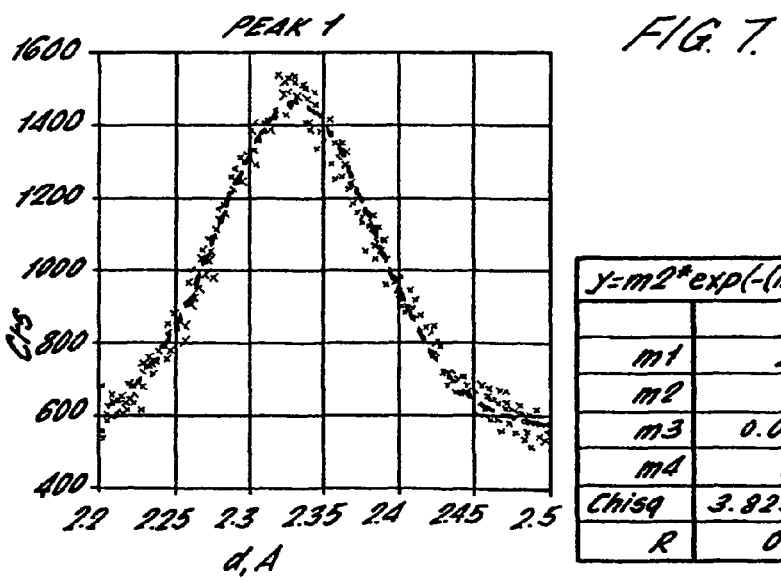
FIG. 7 shows a Gaussian fit to the Al diffraction peak 1 (the box on the right gives the values and errors of the parameters)

Here m0 is the argument (lattice spacing) and m1 to m4 are the function parameters that are sought. The values of the parameters given above represent the initial guesses. The result of fitting is shown in FIG. 7: Gaussian fit to the Al diffraction peak 1. The box on the right gives the values and errors of the parameters.

The fitting result corresponds to a strain accuracy of $\Delta d/d = 0.00033441/2.3304 = 145 \times 10^{-6}$. This corresponds to a stress accuracy of about 10 MPa in aluminium, 14.5 MPa in copper, and 29 MPa in steel.

Figure 8:
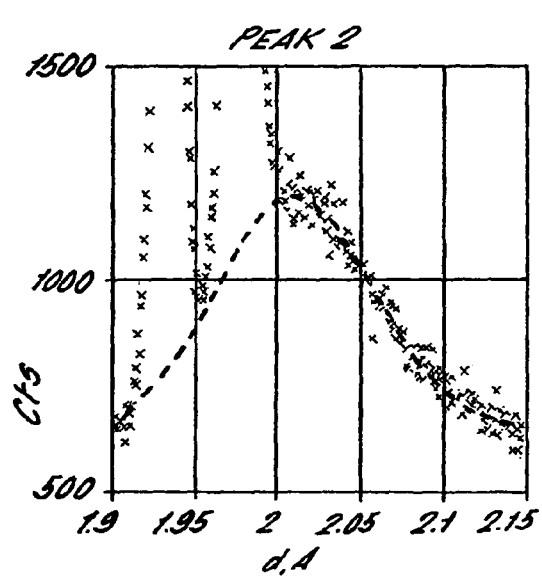
FIG. 8 shows a Gaussian fit to the Al diffraction peak 2 (the box on the right gives the values and errors of the parameters)

The lattice spacing of 2.330 Å is close to the value of $4.05/\sqrt{3} = 2.338$ Å for the (111) reflection in Al. The next reflection, (200), is expected at a lattice spacing of $4.05/2 = 2.025$ Å. Close inspection of FIG. 6 does indeed show that a peak exists at approximately 2 Å in that pattern, but is overlapped by a characteristic twin of lead. However, provided this twin is ignored in the analysis, this peak can be fitted as well, as shown in FIG. 8: Gaussian fit to the Al diffraction peak 2. The box on the right gives the values and errors of the parameters.

The fitting result for peak 2 corresponds to a strain accuracy of $\Delta d/d = 0.0013964/2.0105 = 700 \times 10^{-6}$. This corresponds to a stress accuracy of about 50 MPa in aluminium, 70 MPa in copper, and 140 MPa in steel. The accuracy is affected by the overlap with the characteristic twin of Pb. Information from multiple peaks may be combined to improve the overall accuracy.

The lattice spacing of 2.01 Å is close to the value of 2.025 Å for the (200) reflection in Al. The ratio of the spacing for the two peaks is 1.15, which is very close to the theoretically expected value of 1.156 for the face centred cubic (fcc) lattice.

This Example demonstrates that the accuracy of, lattice parameter determination is adequate for engineering stress measurement applications. The rate of data collection was approximately 15 minutes per pattern.

Figure 9:
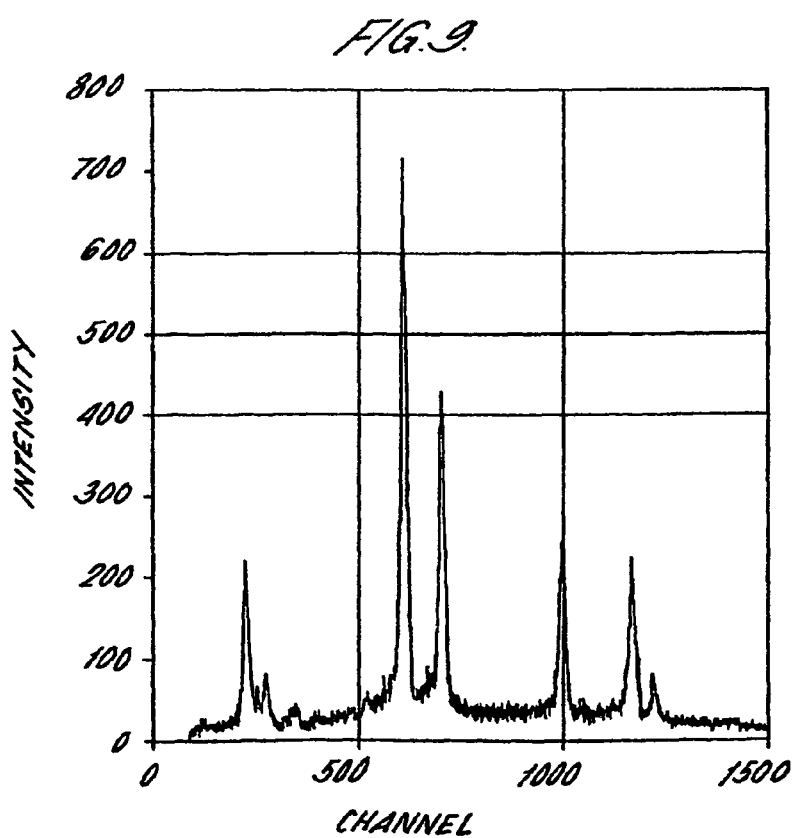
FIG. 9 shows an example of a multiple peak pattern that can be obtained from an aluminium alloy sample.

The method allows very efficient treatment of multiple peak diffraction patterns. An example of a multiple peak pattern that can be obtained from an aluminium alloy sample is shown in FIG. 9. Whole pattern fitting can be applied to extract extremely accurate values of the lattice parameter (better than $5 \times 10^{-5}$) and hence residual lattice strain.

In the present invention, polychromatic beam/energy dispersive detector X-ray transmission experiments are used to analyse polycrystalline engineering materials and components.

The present invention provides a method of accurately determining the lattice parameter and thus stress measurements within the bulk of polycrystalline engineering materials and components. The present invention enables quantitative measurements of stresses (and preferred orientation) in components. This may be achieved by accurate determination of centre positions and intensities of multiple diffraction peaks, not just their identification. The entire (or substantially the entire) diffraction pattern that has been collected may be analysed.

High energy X-rays are used to penetrate a component or sample at very low angles (transmission). Accurate beam collimation helps achieve the resolution required for three-dimensional mapping of stresses. During this procedure, the component or sample may be maintained stationary, while an X-ray probe is moved around it. The probe comprises the X-ray source and detector fixed on a rigid arm thereby maintaining their relative positions fixed.

The invention claimed is:
1. An X-ray diffraction method for the analysis of polycrystalline materials, the method comprising:
    (a) providing a polycrystalline material for analysis;

(b) providing a polychromatic X-ray source, wherein the source produces X-rays by accelerating charged particles to energies of no more than 1 MeV;

(c) collimating X-rays from the polychromatic X-ray source into a beam having a divergence in the range of from $10^{-4}$ to $10^{-2}$ radians;

(d) exposing at least a portion of the polycrystalline material to the collimated X-ray beam, whereby the beam is diffracted;

(e) collecting at least some of the diffracted X-rays in an energy dispersive X-ray detector or array; and (f) analyzing the collected, diffracted x-rays;

(g) quantitatively mapping a lattice parameter in the polycrystalline material using said analyzed, collected, diffracted x-rays.

2. A method as claimed in claim 1, wherein the source produces X-rays by accelerating charged particles to energies of no more than 500 keV.

3. A method as claimed in claim 1, wherein the energy dispersive X-ray detector has a relative energy resolution of from $0.5 \times 10^{-2}$ to $5 \times 10^{-2}$.

4. A method as claimed in claim 1, wherein the energy of the collimated X-ray beam is $\geq 60$ keV.

5. A method as claimed in claim 1, wherein the collimated X-ray beam penetrates the polycrystalline material to an attenuation depth of $\geq 1$ mm.

6. A method as claimed in claim 1, further comprising moving the collimated X-ray beam relative to the polycrystalline material.

7. A method as claimed in claim 6, comprising scanning the collimated X-ray beam across at least a portion of the polycrystalline material, while keeping the polycrystalline material stationary.

8. A method as claimed in claim 1, wherein the collected, diffracted X-rays are analysed in order to determine a structural and/or chemical characteristic of the polycrystalline material.

9. A method as claimed in claim 8, wherein the structural characteristic is the lattice parameter.

10. A method as claimed in claim 9, wherein lattice parameter determination is used to provide information on phase distributions, stresses and/or strains in the polycrystalline material.

11. A method as claimed in claim 10, wherein lattice parameter determination is used to map phase distributions, stresses and/or strains in the polycrystalline material.

12. A method as claimed in claim 11, wherein lattice parameter determination is used to map phase distributions, stresses and/or strains in the polycrystalline material at a depth of $\geq 1$ mm.

13. A method as claimed in claim 1, wherein the polycrystalline material is an engineering article or component part thereof.

14. A method as claimed in claim 1, wherein the polycrystalline material comprises a metal or alloy, ceramic or crystalline polymer, including combinations of two or more thereof.

15. A method as claimed in claim 1, wherein the polycrystalline material is a composite material comprising a crystalline phase.

16. A method as claimed in claim 15, wherein the metal matrix composite material is a glass and/or ceramic reinforced metal matrix composite material.

17. A method as claimed in claim 1, wherein said portion of the polycrystalline material has a thickness of $\geq 1$ mm.

18. An apparatus for X-ray diffraction analysis of polycrystalline materials, the apparatus comprising:
 (i) a polychromatic X-ray source, wherein the source produces X-rays by accelerating charged particles to energies of no more than 1 MeV;
 (ii) means for collimating X-rays from the polychromatic X-ray source into a beam having a divergence in the range of from $10^{-4}$ to $10^{-2}$ radians;
 (iii) an energy dispersive X-ray detector or array for collecting at least some of the diffracted X-rays resulting, in use, from exposing at least a portion of a polycrystalline material to the collimated X-ray beam; and
 (iv) means for analyzing the collected, diffracted x-rays;
 (v) means for quantitatively mapping a lattice parameter in the polycrystalline material using said analyzed, collected, diffracted x-rays.

19. An apparatus as claimed in claim 18, wherein the polychromatic source is moveable with respect to a polycrystalline material to be analysed.

20. An apparatus as claimed in claim 18, wherein the collimated X-ray beam is adapted, in use, to scan, across the polycrystalline material, while the polycrystalline material is maintained stationary.

21. A method of quantitatively mapping the sub-surface distribution of the crystal lattice parameter in a polycrystalline material, the method comprising:
 (a) providing a sample for analysis, wherein the sample comprises a polycrystalline material;
 (b) providing a polychromatic X-ray source, wherein the source produces X-rays by accelerating charged particles to energies of no more than 1 MeV;
 (c) collimating X-rays from the polychromatic X-ray source into a beam having a divergence in the range of from $10^{-4}$ to $10^{-2}$ radians, and a penetration depth of $\geq 1$ mm
 (d) scanning the collimated X-ray beam across the sample, whereby the beam is diffracted;
 (e) collecting at least some of the diffracted X-rays in an energy dispersive X-ray detector or array; and
 (f) analysing the collected, diffracted X-rays to map the lattice parameter in the polycrystalline material.

22. A method as claimed in claim 21, wherein the polycrystalline material is a natural material or an engineering material, including a component formed therefrom.

23. A method as claimed in claim 21, further including:
 (g) transforming the map of the lattice parameter into a map of sub-surface engineering stresses and/or strains.

24. A method as claimed in claim 4, wherein the energy of the collimated X-ray beam has a range of from 100 to 300 KeV.

* * * * *